United States Patent
Wieringa et al.

(10) Patent No.: US 7,748,252 B2
(45) Date of Patent: Jul. 6, 2010

(54) PHANTOM DEVICE

(75) Inventors: Fokko Pieter Wieringa, Duiven (NL); Dirkjan Bakker, Alphen aan den Rijn (NL); René Gerardus Maria Melick, Marken (NL)

(73) Assignee: Nederlandse Organisatie voor toegepast-natuurwetenschappelijk Onderzoek TNO, Delft (NL)

( * ) Notice: Subject to any disclaimer, the term of this patent is extended or adjusted under 35 U.S.C. 154(b) by 299 days.

(21) Appl. No.: 11/915,548

(22) PCT Filed: May 17, 2006

(86) PCT No.: PCT/NL2006/000252

§ 371 (c)(1),
(2), (4) Date: Feb. 25, 2008

(87) PCT Pub. No.: WO2006/126871

PCT Pub. Date: Nov. 30, 2006

(65) Prior Publication Data

US 2008/0214936 A1    Sep. 4, 2008

(30) Foreign Application Priority Data

May 27, 2005   (EP)   ................... 05076253

(51) Int. Cl.
*G01N 29/00* (2006.01)
(52) U.S. Cl. ........................................... 73/1.86
(58) Field of Classification Search .............. 73/1.86
See application file for complete search history.

(56) References Cited

U.S. PATENT DOCUMENTS

| 4,894,013 | A  | * | 1/1990 | Smith et al. ............... 434/268 |
| 5,416,575 | A  |   | 5/1995 | Schwartz et al. |
| 6,400,973 | B1 |   | 6/2002 | Winter |
| 2005/0191331 | A1 | * | 9/2005 | Hunter et al. ............... 424/423 |

OTHER PUBLICATIONS

International Search Report for PCT/NL2006/000252 dated Aug. 2, 2006.

* cited by examiner

*Primary Examiner*—Hezron Williams
*Assistant Examiner*—Rodney T Frank
(74) *Attorney, Agent, or Firm*—Leydig, Voit & Mayer, Ltd.

(57) ABSTRACT

A phantom device for mimicking anatomical structures, comprising: at least one electronic device layer comprising segmented areas of liquid crystals for forming a graphic layout of an anatomical structure; the segments comprising dyes of various absorbing characteristics for mimicking anatomical structures such as blood vessels; the areas further comprising electrically controllable optical diffuser and/or absorber elements for varying the absorption in the segments so as to mimic dynamical properties of said anatomical structure.

14 Claims, 6 Drawing Sheets

PHANTOM DEVICE

FIELD OF THE INVENTION

The invention relates to a phantom device for mimicking anatomical structures.

BACKGROUND

Imaging techniques like photography and filming using visible, infrared or ultraviolet optical radiation are generally known in the art and commonly used to image, measure and characterize the surfaces of tissue. Optical imaging techniques have also been described to detect and display anatomical structures buried beneath the surface of biological tissue.

Principles for optical imaging techniques to detect and display the value of physiological parameters (such as heart beat rate, respiratory rate, pulse oximetry, etc) have also been described. Some of these principles offer a combination of anatomical imaging and physiological parameter imaging as for example disclosed in WO10/15597. Said publication discloses an imaging apparatus for imaging buried structures using various infrared wavelengths. The absorption ratios are used to derive the oxygenation of blood and other physiological parameters of interest.

One of the problems associated with said imaging apparatus and other prior art imaging techniques, is that calibration is difficult. For true calibration controlled oxygen studies on volunteers are performed which is costly and laborious. While phantom devices in the art are known to test certain functionality of imaging devices, they are generally static in nature and not reliable to reproduce clinically viable solutions for testing the imaging devices. One known device is described in U.S. Pat. No. 6,400,973. An electronic device is disclosed mimicking an arterial blood pulse using a polymer dispersion liquid crystal device. However, this device is not designed for testing the imaging performance of an imaging apparatus.

SUMMARY OF THE INVENTION

The invention has as one of it's objections to provide a phantom device for mimicking anatomical structures, wherein the imaging performance of an imaging apparatus can be tested and calibrated using predetermined dynamical behavior.

To this end, the invention provides a phantom device according to the features of claim 1. In particular, according to the invention, the phantom device, comprises at least one electronic device layer comprising segmented areas of liquid crystals for forming a graphic layout of an anatomical structure; the segments comprising dyes of various absorbing characteristics for mimicking anatomical structures such as blood vessels; the areas further comprising electrically controllable optical diffuser and/or absorber elements for varying the absorption in the segments so as to mimic dynamical properties of said anatomical structure.

It is noted that the use of pigments in a polymer dispersion liquid crystal device is known from for example EP0434366. However, in this application, the dichromatic pigment is used for homogeneously increasing contrast of a display device.

While the various dyes in the segmented areas mimic multiple DC components corresponding to different stages of for instance oxygenation in blood vessels, the dynamic variation of the absorption may be realized by the scattering crystals, which cause the light to diffuse and vary the translucence of the device.

In one embodiment, the phantom device further comprises a tissue layer covering said at least one electronic device, for mimicking tissue covering said anatomical structure. In particular, preferably, multiple electronic device layers are embedded in tissue layers to mimic the 3D properties of an organic object such as an arm or the like. In its simplest form, the phantom device provides a series of predetermined static and dynamical test parameters which can be measured by an imaging device. Preferably, however, the phantom device comprises an output unit for outputting signals representative for a predetermined dynamical behavior of said phantom device, for calibrating an imaging device for imaging buried structures.

BRIEF DESCRIPTION OF THE DRAWINGS

The invention will be further illustrated with reference to the accompanying drawings. In the figures.

DETAILED DESCRIPTION OF THE DRAWINGS

Figure 1:
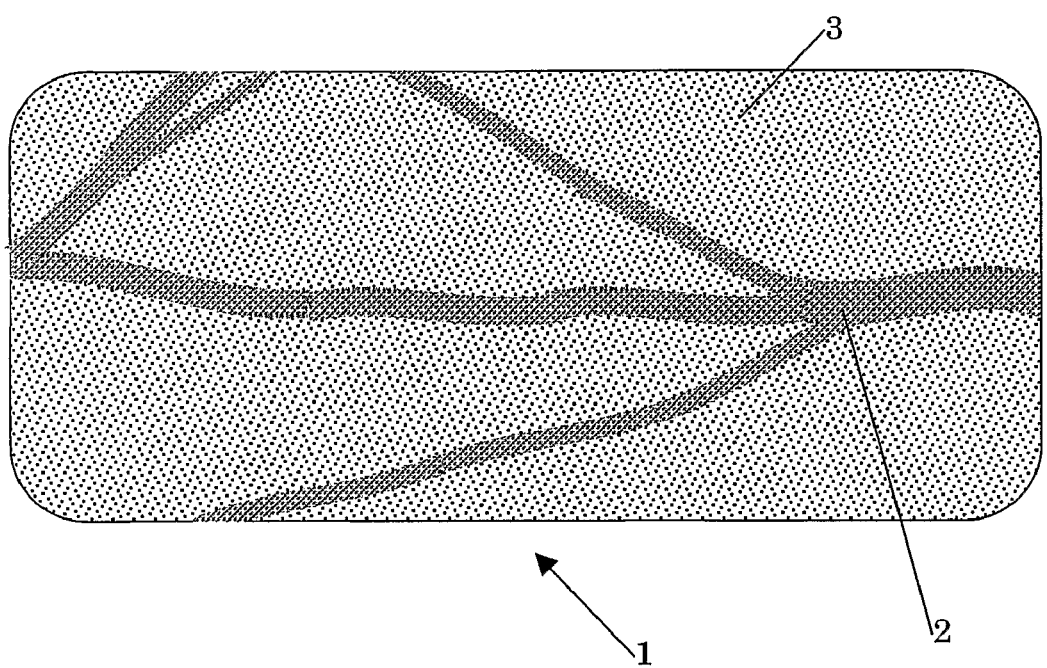
FIG. 1 shows a first embodiment of a phantom device according to the invention.

In the figures, the same or corresponding features will be referenced using the same reference numerals.

In FIG. 1 a phantom device 1 is illustrated having a dyed structure 2 embedded on a substrate 3 to represent realistically a structure of blood vessels in an object such as a human arm. Such as follows from the cross sectional view illustrated in FIG. 2, the dyed structure is preferably covered with a material 4 rendering similar absorption, reflection, scattering and transmission properties similar to normal biological tissue. In this structure, different regions having different optical properties may be present, for example, to represent a fat layer, bones etc.

The dyed structure 2 is provided on a substrate, preferably, a polymer substrate 3 which houses segmented areas that are doted with dyes of various absorbing characteristics for mimicking anatomical structures such as blood vessels to be imaged by a imaging device 5. Furthermore, in the areas electrically controllable optical diffuser and/or absorber elements are provided for varying the absorption in the segments so as to mimic dynamical properties of said anatomical structure. In one embodiment, the dyed areas are provided with boundaries that are formed by conductive zones for forming an electrodes. In this way, the diffuser/absorber elements can be electrically controlled to vary the diffusing/scattering properties of the elements. By varying these properties, as a result, the path length of optical radiation used for imaging purposes is varied, resulting in a variation in scattering and/or absorption or other optical characteristics of the dyed area. In this way, dynamic characteristics of blood vessels can be imitated to mimic the pulsating properties of the vessels.

Figure 2:
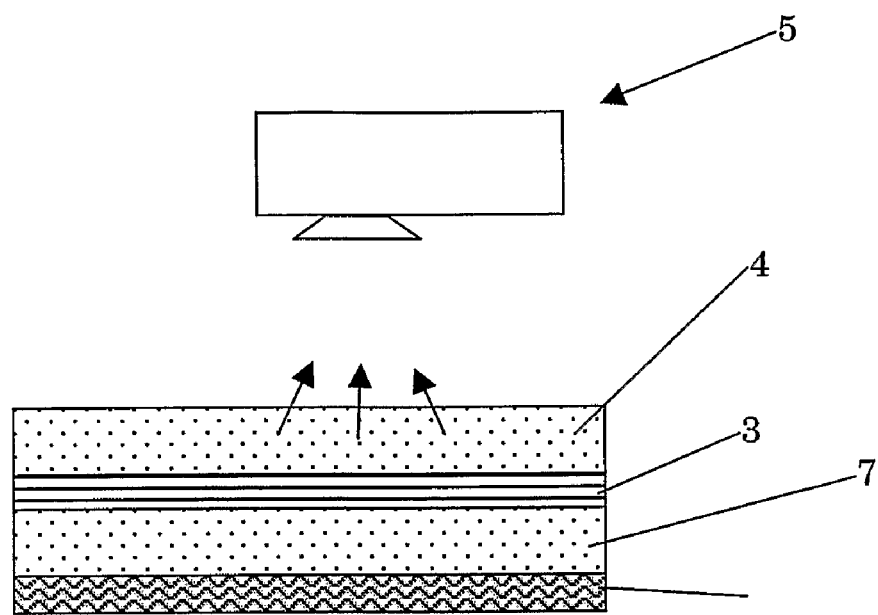
FIG. 2 shows a cross section of the phantom device according to FIG. 1.

Using various sorts of dyes, absorption characteristics can be exactly predetermined, so that a variety of degrees of oxygenation of blood the vessels can mimicked. In particular, venous and arterial blood vessels can be mimicked, wherein, as is illustrated in FIG. 2 the arterial blood vessels may be formed by the deepest electronic device 6 and the venous blood vessels may be formed by the more superficially arranged electronic device 3. Between the devices 3, 6 a tissue layer 7 is provided.

In the electronic devices 1, 6, vessel patterns 2 can be formed by traces filled with a suitable dye mixture. In case of liquid dyes these may be mixed with a liquid crystal fluid. The scattering and absorption properties of the LCDs assigned to different areas can be electrically modulated in a reproducible manner. In the embodiment shown in FIG. 2 two devices each having differing vessel patterns are stacked. The top layer is a diffuse layer having optical properties of a tissue surface, for example, skin, bladder wall, stomach wall, etc. In or upon the top layer, natural chromophores (e.g. melanine) or artificial dyes may be incorporated to imitate e.g. skin color.

Figure 3:
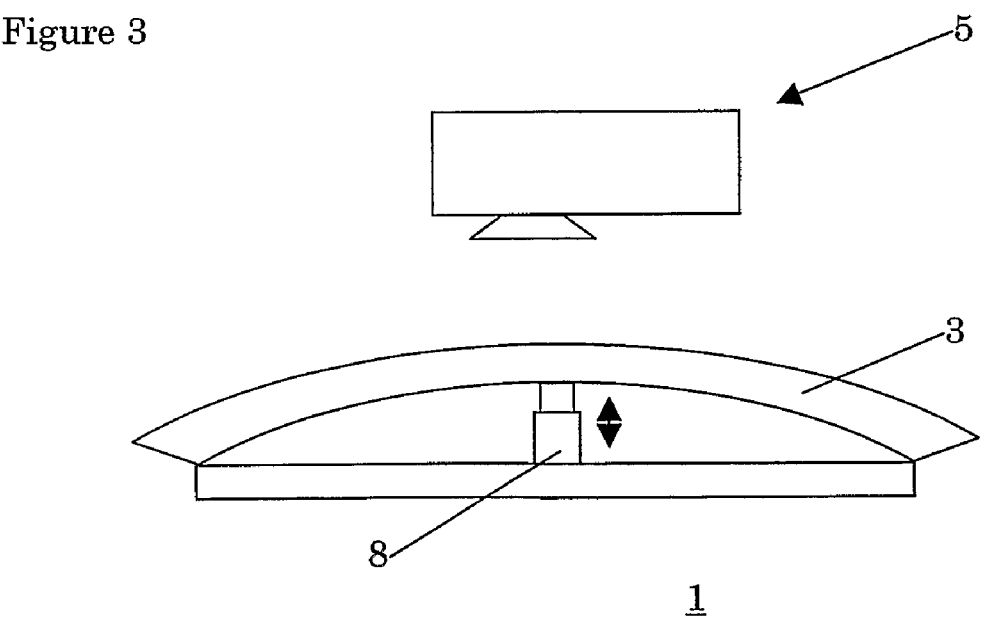
FIG. 3 shows an embodiment where the phantom device is deformable.

FIG. 3 schematically shows a preferred embodiment where the device 1 is deformable and comprises an actuator 8 for deforming said device 1 into predetermined forms. Such an embodiment allows to create dynamic convex or concave distortion of the tissue phantom 1. Defined dynamic behavior of curved surfaces is very important to test the dynamic behavior of the equipment to be tested/calibrated (e.g. alternating reflections on such surfaces can lead to temporal detector saturation).

Further mechanical actuators may be provided that allow well defined movements up to 3 dimensions in space (X, Y and Z axis) as well as over time (controlled speed of movements). For imaging equipment such dynamic features are important to standardize checks and adjustment procedures for artifacts like blurring due to limited frame rate, the accuracy of movement compensation mechanisms, etc.

Figure 4:
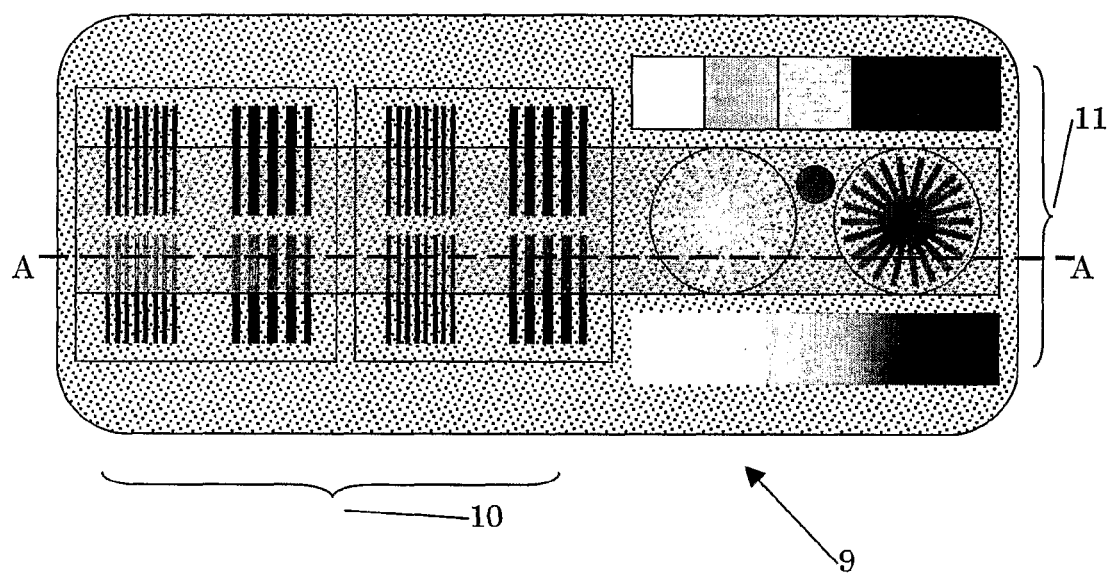
FIG. 4 shows a second embodiment of a phantom device according to the invention.
Figure 5:
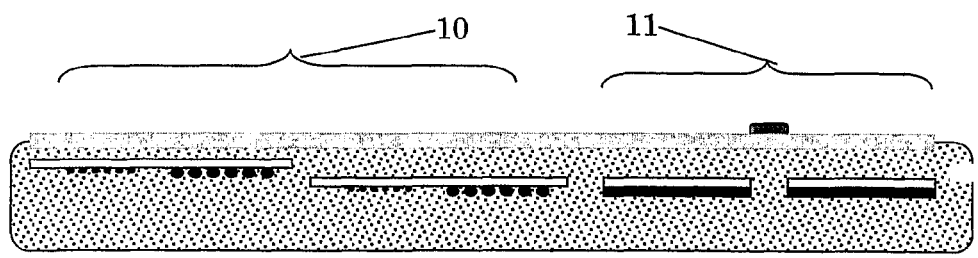
FIG. 5 shows a cross section of the phantom device according to FIG. 4 along line A-A.

FIG. 4 shows an alternative embodiment of a phantom device 9 according to the invention. In this device, the segmented areas comprise test patterns 10, 11 for testing a resolving power of a imaging device for imaging buried structures. The test patterns 10 as will be apparent from the cross sectional view of FIG. 5 may be provided on different depths of the phantom device 9. In another (not shown) embodiment, a pattern may be provided, so that the tissue layer is increasing in thickness. With such a test pattern, a maximum penetration depth can be determined for the imaging apparatus.

As illustrated, several test patterns (e.g. parallel line pairs 10 and/or fanned beams 11 at various pitches and with various spectral behavior) are embedded in a tissue-like optical material. Electrically controllable LCD-devices can be combined with these test patterns in order to add physiological signals (e.g. respiration and heartbeat). Also a spectrally neutral gray scale and a reference color pattern (incl. IR) may be incorporated. The test patterns 10, 11 may have well known 3-dimensional shapes and patterns (e.g. slits, trenches, cylinders, etc.). The external and internal surfaces of the device 9 can have an irregular shape that closely matches a part of the body.

The phantom can be used as a reference or training tool in combination with devices that enable the imaging of buried structures like blood vessels. On the phantom a region of a soft material, suitable for puncturing (e.g. with a needle) may be used in combination with an underlying target (e.g. a vessel pattern). This would allow users to practice their surgical, injection or blood withdrawal skills. It would also be a well defined and repeatable method to compare the functional parameters of different devices for imaging beneath the tissue surface.

Figure 6:
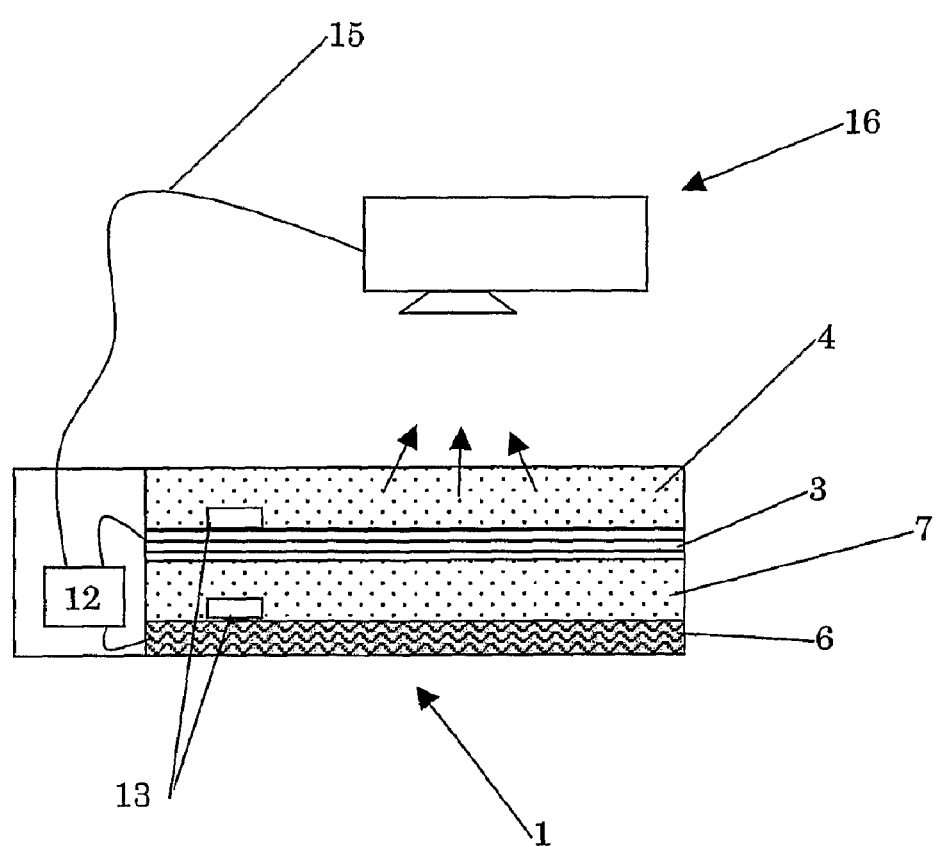
FIG. 6 shows another embodiment of the phantom according to the invention.

FIG. 6 shows that the phantom 1 can be equipped with a central processing unit 12, one or more optical detectors 13, connections offering physiological reference signals 14 and a means of communication 15 with the device 16 to be calibrated or tested. Some devices that optically extract physiological parameters from tissue are designed to make use of an accepted clinical parameter by methods generally known in the art.

Figure 7:
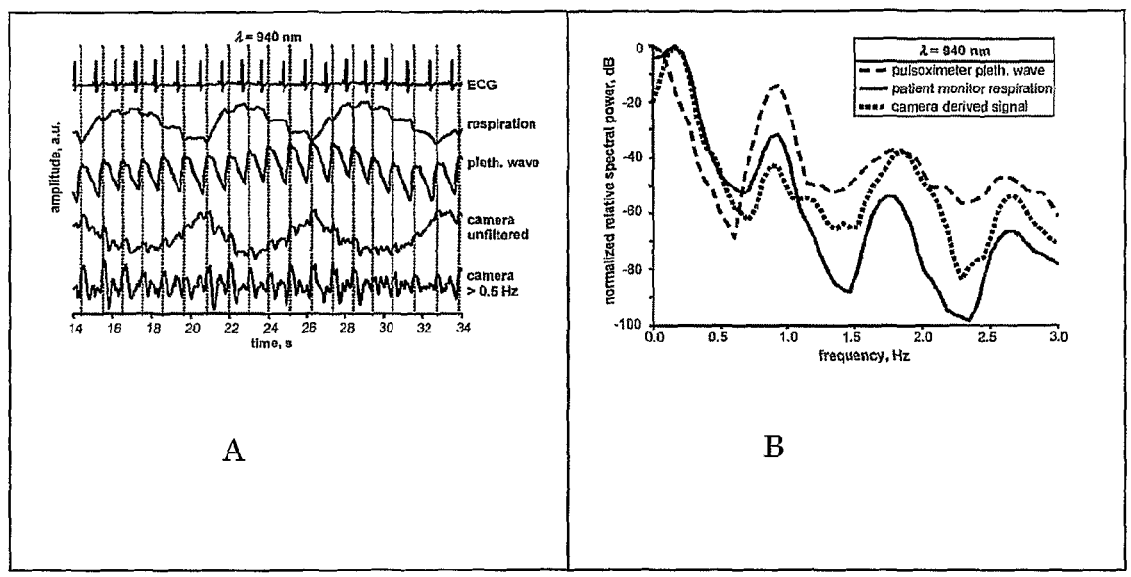
FIG. 7 shows a system of a phantom device according to the invention and an imaging device to be calibrated.

Typically this would be physiological registrations as illustrated in FIG. 7 of Electro Cardio Grams (ECG), a photoplethysmographic trace as derived from a traditional pulse oximeter, a respiration signal from a ventilator or patient monitor, dynamic blood pressure, and the like. In particular, FIG. 7A shows an example of reflectance mode photoplethysmographic signals derived from a camera (lower two traces). The upper three traces are reference signals obtained using clinical devices (HP-patient monitor and Nellcor pulse oximeter). FIG. 7B shows Fourier spectra of two reference traces (respiration and pulse oximeter plethysmographic output) compared to a camera-derived signal.

The device already needs to generate signals like these in order to modulate the LCD-devices, which also allows to make these signals externally available using standard connections as accepted by the field. By not only presenting these signals but also their setting values (e.g. using a digital communication protocol) an automatic calibration can be performed.

Even if automatic adjustment is not desired, the phantom can provide comparison between a stored waveform or image and the actually obtained waveform or image. Automatic recognition of devices that are compatible (and of those that are non-compatible) with the phantom can be achieved by the aforementioned communication bus and/or by comparing signals received by optical detectors in the phantom with reference parameters (i.e. if via a communication bus the device would present itself as a model X but send out a different characteristic wavelength or modulation, then compatibility is not warranted and e.g. an error message could be displayed.

Figure 8:
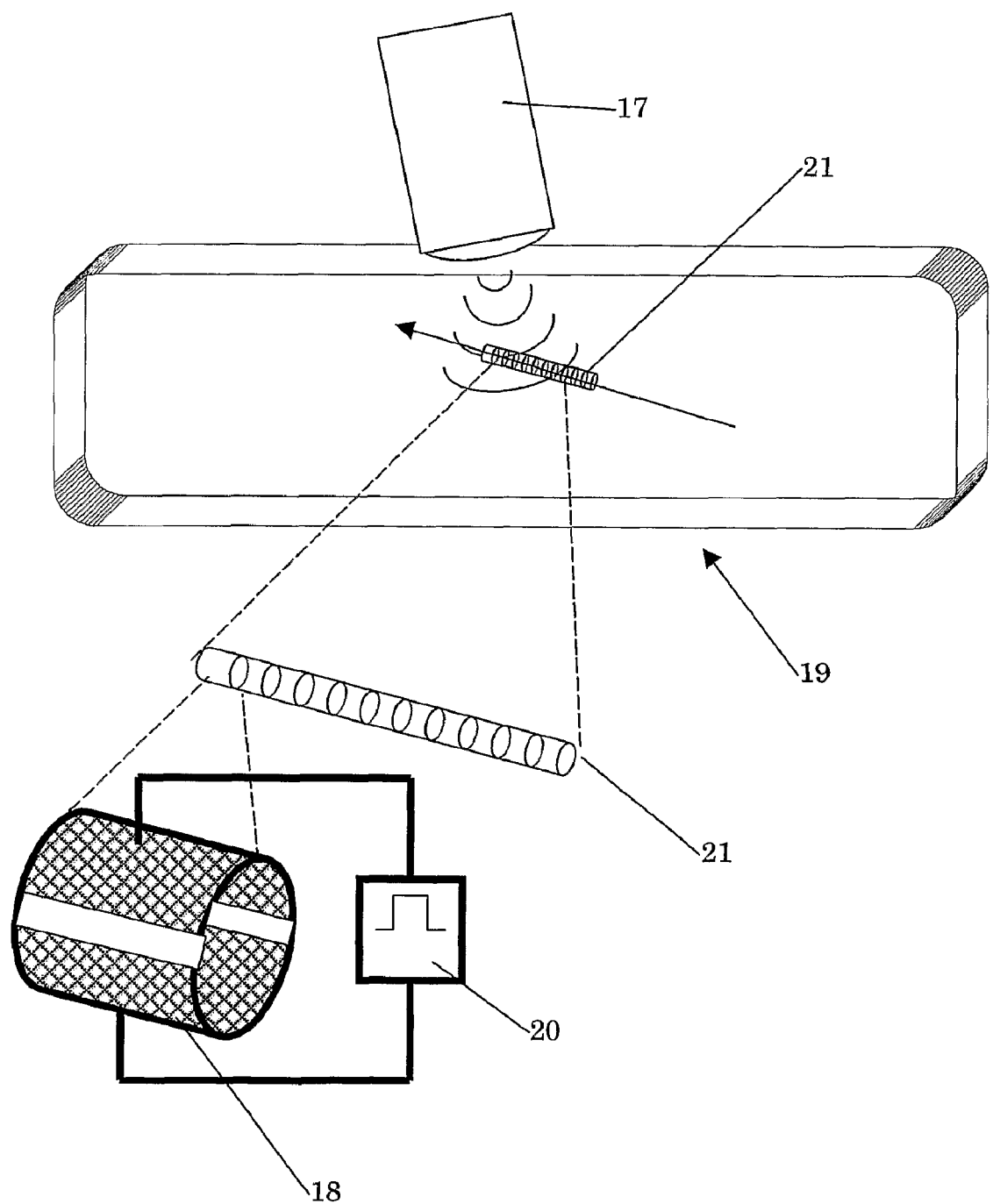
FIG. 8 shows another imaging device to be calibrated by a phantom device according to the invention.

FIG. 8 shows another imaging device to be calibrated. In particular, the imaging device is an ultrasound imaging device 17 since it has been found that the electronically orientable crystals 18 of the liquid crystal device 19 are also effective in varying the acoustic properties of the phantom device. Indeed it can be shown that in the phantom device, when electrically controlled by a controller 20, the scattering behaviour of liquid crystal materials also varies for ultrasonic waves and it is thus possible to construct a 3-dimensional array of individually controllable ultrasound scattering volume elements.

In traditional ultrasound phantoms a dynamic scattering behaviour can be achieved using a liquid or gel filled phantom with interchangeable mechanical parts, liquids or gels. Such devices are not very stable and difficult to transport.

In contrast, the liquid crystal devices such as PDLCs are very stable and behave like solid state components. Their reproducibility is excellent and individually controllable segments can be integrated into complex detailed 3-dimensional structures ("holographic structure simulators").

3D-structures 21 (as seen in FIG. 8, mimicking a 3D blood vessel or also as shaped as described previously in this patent application in the section about optical behaviour) with variable known scattering properties can be used as a calibration tool for general echoscopic imaging devices.

Due to the continuous variability of scattering behaviour from non-scattering liquid to scattering liquid, the contrast level for discerning contrast between various structures can be determined. This contrast level is an indicator of echoscopic imaging quality.

The PDLC technique is also highly applicable for the calibration of harmonic ultrasound imaging devices (which use non-linear scattering behaviour to form an image). A typical application would e.g. be a bladderscan calibration phantom with stepwise variable scattering levels of the liquid volume within the simulated bladder.

PDLC technology can also be used to calibrate doppler ultrasound devices. By sequentially varying the scatter behaviour of a large amount of PDLC elements placed in a line, the propagation of a pulsating bloodflow can be imitated. Since the pitch of segments and timing of segment excitation can be controlled very accurately, a well determined time/speed profile can be generated for the simulated pulsating flow.

Existing calibration devices for doppler systems pump a suspension of micro-particles (e.g. latex spheres) through a liquid or gel phantom. These devices are cumbersome because the particles tend to clutter and portability is very restricted.

The invention claimed is:

1. A phantom device for mimicking anatomical structures, comprising:
   at least one electronic device layer comprising segmented areas for forming a graphic layout of an anatomical structure; wherein the segmented areas comprise dyes of various absorbing characteristics for mimicking anatomical structures such as blood vessels; and wherein the segmented areas further comprise orientable diffuser and/or absorber elements for varying the optical and/or ultrasonic absorption in the segmented areas so as to mimic dynamical properties of said anatomical structure.

2. A phantom device according to claim 1, further comprising a tissue layer, covering said at least one electronic device, for mimicking tissue covering said anatomical structure.

3. A phantom device according to claim 1, further comprising multiple electronic device layers embedded in tissue layers.

4. A phantom device according to claim 2, wherein said tissue layer is increasing in thickness from one side to another.

5. A phantom device according to claim 1, wherein said segmented areas comprise test patterns for testing a resolving power of an imaging device for imaging buried structures.

6. A phantom device according to claim 1, wherein said device is deformable and comprises an actuator for deforming said device into predetermined forms.

7. A phantom device according to claim 1, wherein said electronic device layer comprises a polymer dispersion liquid crystal device.

8. A phantom device according to claim 1, further comprising an output unit for outputting signals representative for a predetermined dynamical behavior of said phantom device, for calibrating an imaging device for imaging buried structures.

9. A system comprising:
   an imaging device for imaging buried structures; and
   a phantom device for mimicking anatomical structures, the phantom device comprising:
      at least one electronic device layer comprising segmented areas for forming a graphic layout of an anatomical structure,
      wherein the segmented areas comprise dyes of various absorbing characteristics for mimicking anatomical structures such as blood vessels,
      wherein the segmented areas further comprise orientable diffuser and/or absorber elements for varying the optical and/or ultrasonic absorption in the segmented areas so as to mimic dynamical properties of said anatomical structure,
      wherein the phantom device further comprises an output unit for providing output signals representative for a predetermined dynamical behavior of said phantom device, for calibrating an imaging device for imaging buried structures; and
   wherein said imaging device comprises an input for receiving said output signals and a unit for adjusting a calibration of said imaging device based on said output signals.

10. A system according to claim 9 wherein said imaging device is an infrared camera.

11. A system according to claim 9, wherein said imaging device is an ultrasound imaging device.

12. A system according to claim 11, wherein the ultrasound imaging device is from a set of devices consisting of: a harmonic ultrasound imaging device, and a doppler ultrasound device.

13. A method of calibrating an ultrasound imaging device, the method comprising:
   placing within a field of view of the ultrasound imaging device at least one electronic device layer comprising orientable diffuser and/or absorber segments for varying ultrasonic absorption in the segments so as to mimic dynamical properties of an anatomical structure; and
   operating the ultrasound imaging device to render an image of the at least one electronic device layer.

14. A method according to claim 13, further comprising: sequentially varying an absorbing characteristic of adjacent liquid crystal elements that are formed in a 2D or 3D region mimicking a blood vessel, for mimicking a blood flow within the blood vessel.

* * * * *